United States Patent [19]

Franetzki et al.

[11] 4,051,843
[45] Oct. 4, 1977

[54] APPARATUS FOR THE DETERMINATION OF THE RESPIRATORY PASSAGEWAY RESISTANCE

[75] Inventors: Manfred Franetzki, Erlangen; Volker Korn, Nuremberg; Karl Prestele, Erlangen, all of Germany

[73] Assignee: Siemens Aktiengesellschaft, Berlin & Munich, Germany

[21] Appl. No.: 660,031

[22] Filed: Feb. 20, 1976

[30] Foreign Application Priority Data

Feb. 26, 1975  Germany ............................ 2508319

[51] Int. Cl.² .............................................. A61B 5/08
[52] U.S. Cl. ................................................ 128/2.08
[58] Field of Search ............. 128/2.08, 2.07, DIG. 29

[56] References Cited

U.S. PATENT DOCUMENTS

| 1,817,145 | 8/1931 | Hobart | 128/2.08 |
| 3,036,569 | 5/1962 | Clements et al. | 128/2.08 |
| 3,598,111 | 8/1971 | Kahn et al. | 128/2.08 |
| 3,726,271 | 4/1973 | Mondshine et al. | 128/2.08 |
| 3,857,385 | 12/1974 | Hampl | 128/2.08 |
| 3,903,742 | 9/1975 | Colton | 128/2.08 X |
| 3,949,739 | 4/1976 | Rodder | 128/2.08 |
| 3,960,142 | 6/1976 | Elliot et al. | 128/2.08 |

FOREIGN PATENT DOCUMENTS

| 2,233,829 | 3/1974 | Germany | 128/2.08 |
| 1,466,936 | 5/1969 | Germany | 128/2.08 |

Primary Examiner—Robert W. Michell
Assistant Examiner—Lee S. Cohen
Attorney, Agent, or Firm—Hill, Gross, Simpson, Van Santen, Steadman, Chiara & Simpson

[57] ABSTRACT

An apparatus for the determination of the respiratory passageway resistance. Apparatus of that type in general evidence a flow resistance located in the respiratory passageway, whose resistance value is periodically varied at a frequency which is located above the breathing frequency, or a breathing tube with a flow resistance and a pulse generator for subjecting the breath flow with higher-frequencied pressure- or, respectively flow pulsations.

10 Claims, 3 Drawing Figures

APPARATUS FOR THE DETERMINATION OF THE RESPIRATORY PASSAGEWAY RESISTANCE

FIELD OF THE INVENTION

The present invention relates to an apparatus for the determination of the respiratory passageway resistance. Apparatus of that type in general evidences a flow resistance located in the respiratory passageway, whose resistance value is periodically varied at a frequency which is located above the breathing frequency, or a breathing tube with a flow resistance and a pulse generator for subjecting the breath flow with higher-frequencied pressure- or, respectively, flow pulsations.

DISCUSSION OF THE PRIOR ART

An apparatus of this type is known, in which the breathing resistance periodically has a supplementary or additional resistance switched thereto or, respectively, away therefrom. Through measurement of the pressure drop-off with and without the additional resistance there may be obtained the respiratory passageway resistance. Moreover, there is known an apparatus of the above-mentioned type in which the breath flow has pressure fluctuations of about 3 Hz superposed thereon by means of a piston pump, and wherein a variable flow resistance which is located at the other side of the breathing tube is varied for so long until a differential pressure measuring apparatus, which is connected to the breathing tube on both sides of the connections for the piston pump, indicates the value zero. The value of the flow resistance is then a direct measure for the respiratory passageway resistance.

The respiratory passageway resistances which are to be determined pursuant to these measuring principles are, however, not sufficiently exact, since it is neglected that the respiratory passageway resistance represents a complex flow resistance, constituted of an actual or real portion, the so-called alternating flow resistance, and an imaginary component formed by capacitive and inductive elements. It has hereby been proposed that, for alternating measurements with apparatus of the above-mentioned type, there be provided measuring means which can separately determine the real and imaginary components of the respiratory passageway resistance, and also facilitate phase measurements. Hereby, an effective or ohmic resistance is utilized as the flow resistance which, as occasioned, may include a small changeable component with negligible imaginary components. The problem in those types of installations lies in the realization or obtention of a flow-constant effective resistance. Such available capillary sieves, capillary or slit channel packets are subject to dirtying, are difficult to clean, and thereby not constant in their values over extensive periods of time. Moreover, the external effective resistance exerts a considerable burden on the patient during breathing.

SUMMARY OF THE INVENTION

Accordingly, it is an object of the present invention to provide an apparatus of the above-mentioned type which avoids the disadvantages encountered in the prior art. Such an apparatus of the above-mentioned type for determining the respiratory passageway resistance of the above-mentioned type is to be provided which is inexpensive and easily cleansed, which will not burden the patient while breathing, and thereby appears to be suited as an apparatus for series examinations. The foregoing object is inventively attained in that the flow resistance is complex. Within the scope of the invention is is advantageous to select this complex flow resistance so as to be approximately purely inductive, whereby the latter is constructed from an extended or multiple-bent hose, whose cross-section preferably is circular or square. That type of flow resistance is simple to construct, inexpensive and easily cleansed, and burdens breathing less than the effective resistance in the known apparatus.

In an advantageous further feature of the invention, for effecting a periodic change in the flow resistance, the hose length may be varied in conformance with a type of a trombone or telescopically. Moreover, the approximately purely inductive portion of a complex flow resistance may be formed through the intermediary of apparatus in which the streaming air periodically accelerates additional masses, whereby a sufficiently strong and constant coupling must be created between the accelerated air and additional mass, for example, by means of a turbine or a gearwheel volumeter.

The invention was preceded by considerations and investigations as to how for — proceeding from a consistently complex formulation of respiratory passageway resistance, flow resistance and mouth pressure — there could be undertaken simplifications for a technical realization and as what extent phase measurements are actually necessary. Upon considering the fact that the respiratory passageway resistance and flow resistance are connected in parallel, there is obtained the relationship for the sought after complex respiratory passageway resistance $$Z \cdot e^{j\varphi} = \frac{P e^{j\psi} \cdot R e^{j\alpha}}{I \cdot R e^{j\alpha} - P e^{j\psi}} \quad (1)$$

wherein Z, R, P and I designate the amplitudes of the sought after respiratory passageway resistance, the external flow resistance, the pressure which is to be measured, and the impressed flow; and $\phi$, $\alpha$ and $\psi$ designate the associated phase angles. The phase factors signify that there presently occur phase displacements with regard to the alternating flow impressed on the system. Through the utilization of reduced magnitudes $p = P/(I \cdot R)$ and $z = Z/R$, there is obtained from relationship (1) for the amount $z$ and the phase $\phi$ of the respiratory passageway resistance:

$$z = p/\sqrt{1 + p^2 - 2p \cdot (\sin \alpha \sin \psi - \cos \alpha \cos \psi)} \quad (2)$$

$$\phi = \alpha + \psi - \text{arctg} \frac{\sin \alpha - p \cdot \sin \psi}{\cos \alpha - p \cdot \cos \psi} \quad (3)$$

From equations (2) and (3), with consideration of the structure of the pregiven flow resistance, there can be taken off the required relationships which are necessary for the measurement. For the preferred construction as an approximately purely inductive resistance, due to $\alpha = \pi/2$, there is then obtained $$z = p/\sqrt{1 + p^2 - 2p \cdot \sin \psi} \quad (4)$$

$$\phi = \frac{\pi}{2} + \psi - \text{arctg} \frac{p \cdot \sin \psi - 1}{p \cdot \cos \psi} \quad (5)$$

From the values of $p$ and $\psi$ obtained during measurement there may be carried out the calculation of $z$ and $\phi$ and, moreover, the actual or rear and, respectively, imaginary components of the respiratory flow resistance. For this purpose there may be utilized special calculating elements, or also prepared transformation diagrams or charts.

Previous investigations have indicated that in measurements of the respiratory passageway resistance of healthy examined persons, no significant phase displacements took place. In ill examined persons having resistance values above 5 mbar1sec, neglecting of the phase measurement lead to an increase in the measured value, whereby the "diagnostic separation sharpness" was improved. Setting $\phi = 0$, there is obtained from equation (5) since $\psi = p$ and, furthermore $$z = \frac{p}{\sqrt{1 - p^2}} \tag{6}$$

or $$Z = \frac{P}{I \cdot \sqrt{1 - \frac{P^2}{I^2 \cdot R^2}}} \tag{7}$$

Based on the presumption that P is small and R is sufficiently large, there is obtained an approximately linear dependence of the respiratory passageway resistance upon the amplitude of the alternating pressure. The pressure measuring apparatus may then be calibrated in a simple manner to the respiratory passageway resistance.

BRIEF DESCRIPTION OF THE DRAWINGS

Further advantages and details of the invention may now be ascertained from the following detailed description of an exemplary embodiment of the invention, taken in conjunction with the accompanying drawings; in which.

DETAILED DESCRIPTION

Figure 1:
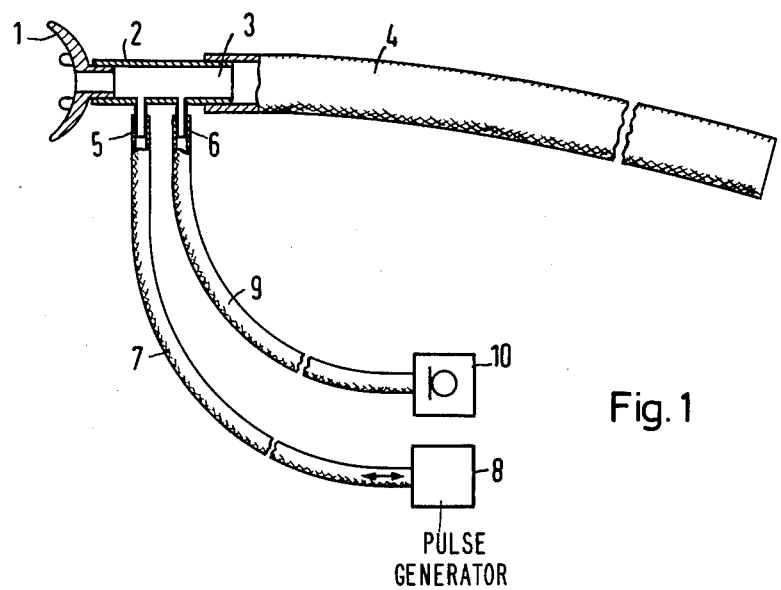
FIG. 1 schematically illustrates an inventive apparatus for the determination of the respiratory passageway resistance.
Figure 2:
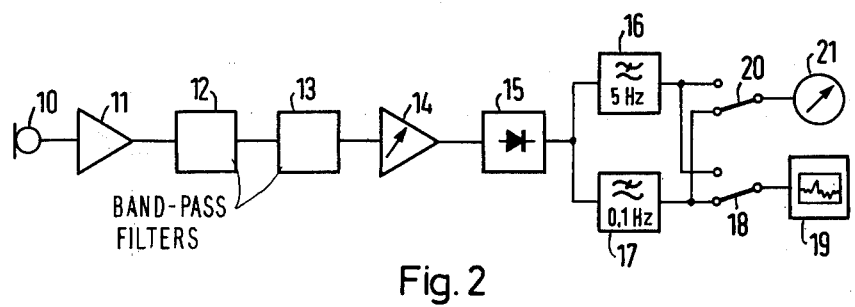
FIG. 2 shows a schematic block circuit diagram of an associated evaluating circuit.

In FIG. 1 of the drawings, a patient mouthpiece is identified by reference numeral 1. Located on the mouthpiece is a connecting element 2, onto whose open end 3 there is attached the blind component of hose 4 formulating the complex flow resistance. The hose has a length of about 1.2 m and an internal diameter of about 1.2 cm. Moreover, located on the connecting piece are two small-diameter connectors 5 and 6, of which the first one is connected with an alternating flow pump 8 through a pneumatic conduit 7, which serves for subjecting the breath flow with flow pulsations which are higher-frequencied in comparison with the breathing frequency. The second connector 6 is connected through a pneumatic conduit 9 with a microphone 10 which serves as a pressure measuring apparatus and transducer. Through suitable electronic means, as shown in FIG. 2, there are filtered out the high-frequency components of the electrical measuring signal which is proportional to the pressure. Connected to and following the microphone 10 is a first amplifier 11 and two sequentially connected band-pass filters 12 and 13 which are set to the pulsating frequency of the alternating flow pump. A further controllable or variable amplifier 14 is followed by a rectifier 15. The rectified measuring signal is transmitted to two parallel-connected low-pass filters 16 and 17, of which the first one is set to 5 Hz and the second to 0.1 Hz as the limiting frequencies. Their output signals may be selectively transmitted across the switch 18 to the time recorder 19, and further, across the switch 20 to the measuring apparatus 21 which is calibrated over to the real or actual respiratory passageway resistance in conformance with the relationship $$Z = \frac{P}{I \cdot \sqrt{1 - \frac{P^2}{I^2 \cdot R^2}}} \tag{7}$$

In that manner there can be alternatively produced and measured the breath-synchronized changes in the respiratory passageway resistance and their timewise median value.

From FIG. 1, it will be seen that the hose 4 has an internal diameter of at most the outer diameter of the breathing tube. For the exemplary dimensions of length (about 1.2m) and internal diameter (about 1.2 cm), the hose 4 has a length of about one hundred times its internal diameter.

Figure 1A:
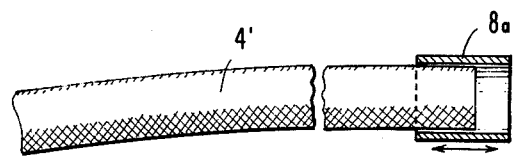
FIG. 1a illustrates a modification of the embodiment of FIG. 1.

As stated in the Summary of the Invention, in an advantageous further feature of the invention, for effecting a periodic change in the flow resistance, the hose length may be varied in conformance with a type of a trombone or telescopically as diagrammatically indicated at 8a in FIG. 1a. FIG. 1a thus shows a hose 4' having a telescopically changeable length for effecting the periodic variation of the flow resistance.

While there has been shown what is considered to be the preferred embodiment of the invention, it will be obvious that modifications may be made which come within the scope of the disclosure of the specification.

What is claimed is:

1. In an apparatus for the quantitative determination of the respiratory passageway resistance including a breathing tube, a flow resistance cooperating with the tube so as to be in the path of the breath flow, pulse generator means for subjecting the breath flow within the tube with higher-frequencied flow pulsations and pressure measuring means for measuring the pressure in said breathing tube, the improvement comprising:
   a. said flow resistance being an elongate tube of predetermined length and internal diameter, which represents the approximately purely inductive part of a definite complex flow resistance with a known value ($Re^{i\alpha}$);
   b. said elongate tube being connected with an open end of the breathing tube;
   c. said pulse generator means being an alternating-flow pressure pump connected with the breathing tube;
   d. said pressure measuring means being set for the frequency of said alternating-flow pressure pump;
   e. and measuring means for indicating the respiratory passageway resistance as a function of said known pulsation flow (I), said known flow resistance (R) and the measured pressure fluctuations (P).

2. An apparatus as claimed in claim 1, said pressure measuring means comprising a pressure transducer connected with the interior of said breathing tube; and frequency filters being serially connected to said transducer which are tuned to the pulsating frequency of said alternating-flow pressure pump.

3. An apparatus as claimed in claim 2, said frequency filters comprising band-pass filters.

4. An apparatus as claimed in claim 1, comprising electronic means for measuring and amplifying the varying pressure amplitude; rectifier means for rectifying said amplified varying pressure amplitude; first and second frequency filters connected to the output of said rectifier means and each receiving said rectified amplitude signal, said measuring means including a time recorder, and means for alternatively connecting said time recorder to the first or second frequency filter so as to enable the alternative representation of breath-synchronized changes in the respiratory passageway resistance and the median value thereof.

5. An apparatus as claimed in claim 4, said first and second frequency filters comprising two low-pass filters having respective limiting frequencies of 5 Hz and 0.1 Hz.

6. An apparatus as claimed in claim 5, said measuring means further including a meter, said alternatively connecting means also serving to alternatively connect said meter to said first and second frequency filters, the output signals of said low-pass filters thereby being alternatively transmitted to said meter.

7. An apparatus as claimed in claim 30, said measuring means being calibrated pursuant to the equation $$Z = \frac{P}{I \cdot \sqrt{1 - \frac{P^2}{I^2 \cdot R^2}}}$$

and said measured value being indicated therein as the respiratory passageway resistance.

8. An apparatus as claimed in claim 1, said elongate tube having an internal diameter of at most the outer diameter of the breathing tube and a length of about 100 times said internal diameter.

9. An apparatus as claimed in claim 1, said elongate tube having a length of about 1.2 m and an internal diameter of about 1.2 cm.

10. In an apparatus for the quantitative determination of the respiratory passageway resistance, including a breathing tube, a flow resistance cooperating with the tube so as to be in the path of the breath flow, means for periodically varying the flow resistance with a frequency lying above the breathing frequency; and pressure measuring means for measuring the pressure in said breathing tube, the improvement comprising;
 a. said flow resistance being an elongate tube of predetermined length and internal diameter, which represents the approximately purely inductive part of a definite complex flow resistance with a known value ($Re^{i\alpha}$);
 b. said elongate tube being connected with an open end of the breathing tube;
 c. said elongate tube having a telescoping structure for effecting the periodic variation of said flow resistance;
 d. said pressure measuring means being set for the frequency at which said flow resistance is periodically varied;
 e. and measuring means for indicating the respiratory passageway resistance as a function of said known variable flow resistance (R), the known variation value of said flow resistance and the measured pressure fluctuations (P).

* * * * *